(12) United States Patent
Spink

(10) Patent No.: US 7,394,552 B2
(45) Date of Patent: Jul. 1, 2008

(54) METHOD FOR MEASURING THE SEPARATION OF EXTENDED OBJECTS IN CONJUNCTION WITH AN OPTICAL OBSERVATION SYSTEM AND MICROSCOPE FOR CARRYING OUT THE SAME

(75) Inventor: Roger Spink, Berneck (CH)

(73) Assignee: Leica Microsystems AG, Heerbrugg (CH)

( * ) Notice: Subject to any disclaimer, the term of this patent is extended or adjusted under 35 U.S.C. 154(b) by 1039 days.

(21) Appl. No.: 10/156,765

(22) Filed: May 29, 2002

(65) Prior Publication Data

US 2003/0011677 A1 Jan. 16, 2003

(30) Foreign Application Priority Data

May 29, 2001 (DE) ................................ 101 25 971

(51) Int. Cl.
*G01B 11/24* (2006.01)
*G01B 11/30* (2006.01)
(52) U.S. Cl. ..................................... 356/603; 250/201.3
(58) Field of Classification Search ................ 356/609, 356/602–604, 623–624; 250/201.3, 201.8, 250/201.6; 359/376
See application file for complete search history.

(56) References Cited

U.S. PATENT DOCUMENTS

| | | | | |
|---|---|---|---|---|
| 4,516,840 A | * | 5/1985 | Nakahashi et al. | 250/201.3 |
| 4,645,347 A | * | 2/1987 | Rioux | 356/609 |
| 4,657,393 A | * | 4/1987 | Stern | 356/609 |
| 4,948,258 A | * | 8/1990 | Caimi | 356/603 |
| 4,991,966 A | | 2/1991 | Raymond | |
| 5,135,309 A | | 8/1992 | Kuchel et al. | |
| 5,359,417 A | * | 10/1994 | Muller et al. | 356/623 |
| 5,448,332 A | | 9/1995 | Sakakibara et al. | |
| 5,545,160 A | * | 8/1996 | O'Rourke | 356/623 |
| 5,737,084 A | * | 4/1998 | Ishihara | 356/609 |
| 5,841,149 A | | 11/1998 | Spink et al. | |
| 5,963,366 A | * | 10/1999 | Nakamura et al. | 359/389 |
| 6,307,636 B1 | * | 10/2001 | Spink | 356/614 |
| 6,407,800 B1 | * | 6/2002 | Shimokawa et al. | 250/201.3 |

FOREIGN PATENT DOCUMENTS

DE 40 07 500 A1 9/1991

(Continued)

OTHER PUBLICATIONS

Adam Technology, "3DM Technology Description," http://members.iinet.net.au/~adamtech/3dm/3dmdescription.html (Jun. 5, 2002).

(Continued)

*Primary Examiner*—Gregory J. Toatley, Jr.
*Assistant Examiner*—Juan D Valentin
(74) *Attorney, Agent, or Firm*—Foley & Lardner LLP

(57) ABSTRACT

Method and device for determining one or more Z distances from an object surface to a reference plane, for example the primary plane of the primary objective of a microscope. By projecting an optical pattern onto an object, and subsequently detecting and computationally evaluating the object's reflection of this pattern by means of an image processing unit, it is possible to obtain relief-like imaging of the object and to identify the individual Z distances, irrespective of the object's contouring.

61 Claims, 8 Drawing Sheets

FOREIGN PATENT DOCUMENTS

| | | |
|---|---|---|
| DE | 44 16 108 A1 | 11/1995 |
| GB | 1073503 | 6/1967 |
| WO | WO 9823989 A1 * | 6/1998 |

OTHER PUBLICATIONS

University of Surrey, "Model Building from 3D Surface Measurements," http://www.ee.surrey.ac.uk/Research/VSSP/3Dvision/model_building/model.htm (Jun. 5, 2002).

Hioki, "Dynamic pattern Projection Method for Measuring Three-Dimensional Scene," http://www.i.h.kyoto-u.ac.jp/~hioki/research/research.html (Jun. 5, 2002).

Opton Co., "Background to 3 dimensional (3D) image recognition based on new Moire method," htp://www.opton.co.jp/techrep/md/md1_/mdel_1.html (Jun. 5, 2002).

Arman et al., "Model-Based Object Recognition in Dense-Range Images—A Review," *ACM Computing Surveys* (Mar. 1993), vol. 25, No. 1, pp. 5-43, http://perso-iti.enst-bretagne.fr/~rouet/these/p5-arman.pdf.

* cited by examiner

METHOD FOR MEASURING THE SEPARATION OF EXTENDED OBJECTS IN CONJUNCTION WITH AN OPTICAL OBSERVATION SYSTEM AND MICROSCOPE FOR CARRYING OUT THE SAME

CROSS REFERENCE TO RELATED PATENT APPLICATIONS

Federal Republic of Germany Priority Application 101 25 971.9, filed May 29, 2001 including the specification, drawings, claims and abstract, is incorporated herein by reference in its entirety.

FIELD OF THE INVENTION

The invention relates to a novel method for determining one or more Z distances from a surface to a reference plane, for example, the primary plane of the primary objective of an optical observation instrument, such as a (stereo) operation microscope, which provides spatial imaging of the object, as well as to a microscope for carrying out such a method.

BACKGROUND OF THE INVENTION

Determining the distance from an operation microscope to an object is very important, especially in surgery—for example in neurosurgical applications, since it is common for operations to be carried out with navigation systems and for the microscope to be used as a non-contact sensor. Once focusing has been carried out successfully via the defined measurement integral, for example, over a limited area around the focal point, a measured value can be sent to the navigation system, processed there and subsequently indexed in the data record of the object, which is generally the patient. In the currently known focusing systems, the working distance which is set once the image sharpness has been optimized is used for determining the working distance between a stereo microscope and the object surface. The evaluation of the image sharpness may be carried out in the entire field of view or in a restricted field of view, for example in a narrowly defined region around the centre of the field of view, normally a substantially point-like region with a diameter of approximately 1 to 2 mm. The focusing is normally carried out via the primary objective.

SUMMARY OF THE INVENTION

The inventor has found that the known systems are disadvantageous in respect to the following points:
a) Methods of this type generally require a minimum degree of object contouring (edge sharpness at the borders) with a corresponding contrast. If this prerequisite is not satisfied, these methods normally fail.
b) In particular, anatomical preparations, for example brain tissue, sometimes show neither well-pronounced contours nor suitable texture with a minimum contrast.
c) The conditions, which are often sufficient, may become unsatisfactory owing to liquids wetting the object, for example washing liquids mixed with blood.
d) It is not possible to identify the Z distances over the entire field of view, or over fairly large regions of the object, i.e. relief-type recording or imaging of the object is not possible.
e) The required focusing via the primary objective may interfere with the user's work owing to changes in the image sharpness.

Different focusing for a further observer and/or a video system is not possible, i.e. it is not possible to involve a second observer with another focal plane.

It is an object of the invention to provide a method which permits accurate determination of object—operation microscope separations even under unfavourable conditions and/or over the entire image field, and which avoids the said disadvantages of known solutions.

This object is achieved by a method which produces an optical pattern by means of a pattern generator, projects this pattern onto the object via insertion into the primary beam path of the microscope, extracts the reflection on the object via the primary beam path and detects it by means of an observation device, for example a camera/CCD, computationally separates this detection into conjugate patterns and identifies the object relief—microscope distance from the topographical position of these conjugate patterns, as well as by a microscope for carrying out the said method.

It is based on the following effect: when the pattern is focused accurately onto the focal plane, the pattern appears as a single pattern; in the event of defocusing, two conjugate patterns are seen.

In a particular refinement, which can also be used independently of the pattern generator, separate optics, independent of the microscope's primary optics, are placed in front of the camera and the Z-identification is carried out using them.

The aforementioned use of a method involving pattern projection onto the object and subsequent detection for determining the focus, and optionally the implementation of further improvements which are referred to below, leads to the improvements listed below being achieved:
 owing to the inventive use of a separate light source (optical pattern), the object does not need to have a minimum degree of contouring;
 contrast problems during the measurement—for example due to liquids—are eliminated;
 it is possible to focus onto all parts of the object—in particular even ones which are in shadow or unilluminated;
 since it has its own light source, the focus measurement is independent of the primary illumination, and in particular independent of the illumination beam's light-wave range which is used;
 owing to the inventive use of optical patterns, it is possible to discriminate reliably against other light phenomena. In the case of large-area patterns, it is furthermore possible to identify the large-area relief of the object and therefore also to focus on different focal planes;
 owing to the inventive use of separate optics for the camera, it is unnecessary to change the focusing of the primary optics in order to identify the focus; the user's work under the microscope is therefore not disturbed.

Although the above text refers to an operation microscope, the invention is nevertheless not restricted thereto, but rather is available to other users of optical devices with range-finding and focusing instruments (e.g. projectors, video cameras and photographic cameras, etc.).

Moirée methods are not covered by the present invention.

The list of references and FIG. 1 to FIG. 8, together with the subject matter described in the claims, are an integral part of the disclosure of this application. Further details and alternative embodiments can hence be found in the description of the figures.

BRIEF DESCRIPTION OF THE DRAWINGS

The figures will be described coherently and comprehensively. The same reference numbers denote the same components, and reference numbers with different indices indicate functionally equivalent components. The figures conceptually show.

DETAILED DESCRIPTION OF THE PREFERRED EMBODIMENTS

Figure 1:
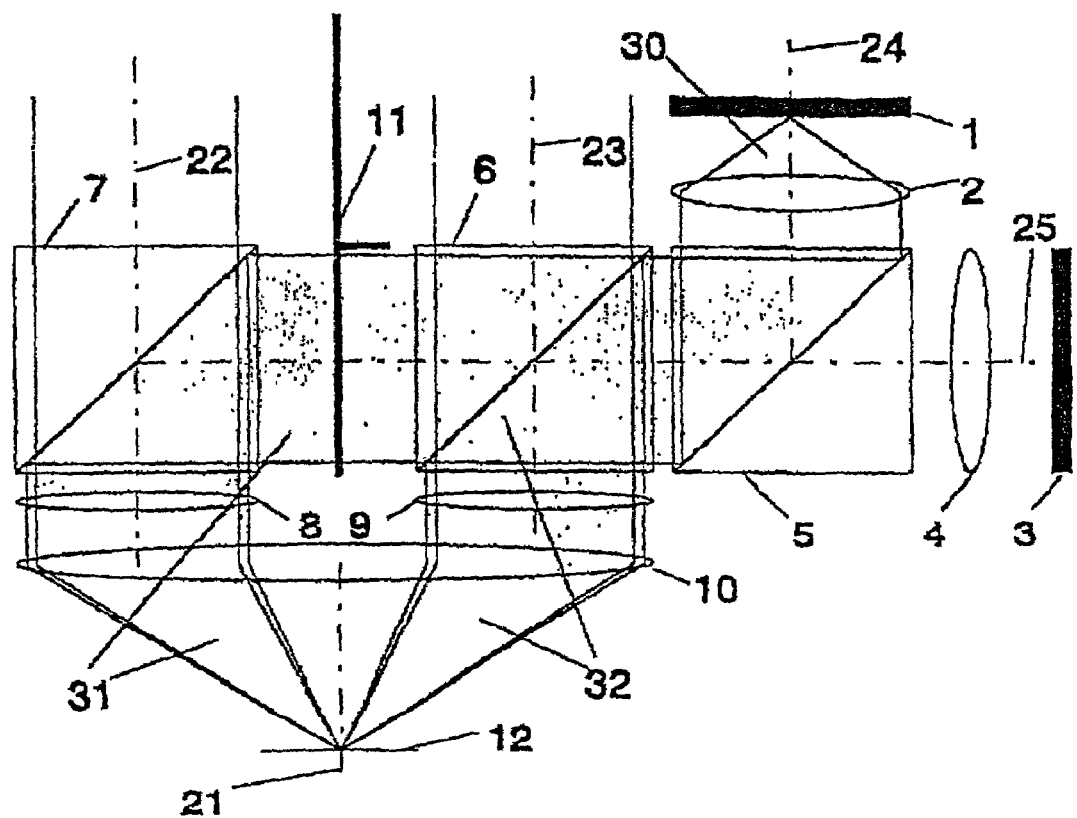
FIG. 1: A symbolic overall structure of an optical observation instrument, for example a stereo operation microscope.

FIG. 1 conceptually shows the overall structure of an optical observation instrument with a pattern generator 1, optics 2 for the pattern generator, a camera 3, for example a CCD, the associated optics 4, a beam splitter 5 for the pattern generator 1, a respective beam splitter 6 and 7 for the insertion and extraction of patterns in the left and right beam path 31/32, zoom optics 8, 9 for the left and right beam path 31/32, a primary objective 10, as well as a shutter 11 for the (temporal) encoding of the pattern elements. Also shown are the object surface 12, the optical axes, specifically 21 for the primary objective 10, for the left and right beam path 22/23, the optical axis 24 of the pattern generator 1, as well as the optical axis 25 with the beam path of the camera 3.

Figure 2:
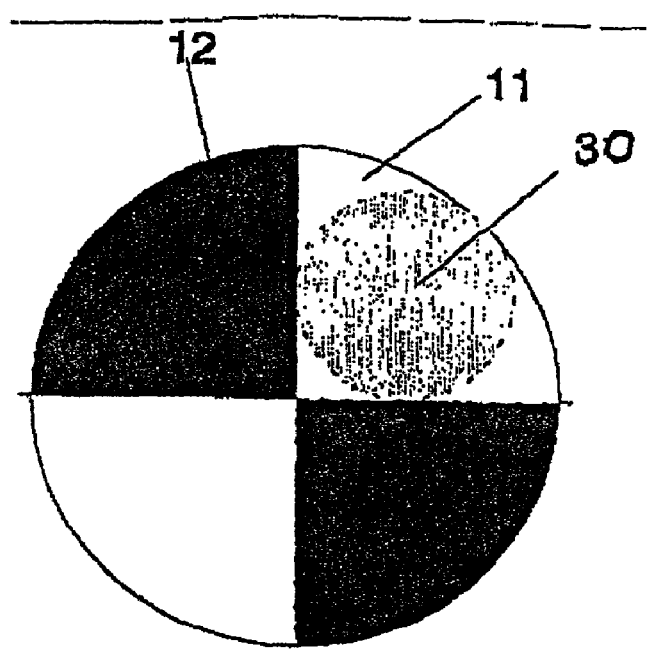
FIG. 2: An example of a shutter for the (temporal) encoding of the pattern elements.

FIG. 2 schematically shows a shutter 11, for example a rotating disc, with the object surface 12 and the inserted beam path 30 of the pattern generator 1 for the (temporal) encoding of the right/left perspective of the pattern, for the purpose of evaluation via a camera 3.

Figure 3:
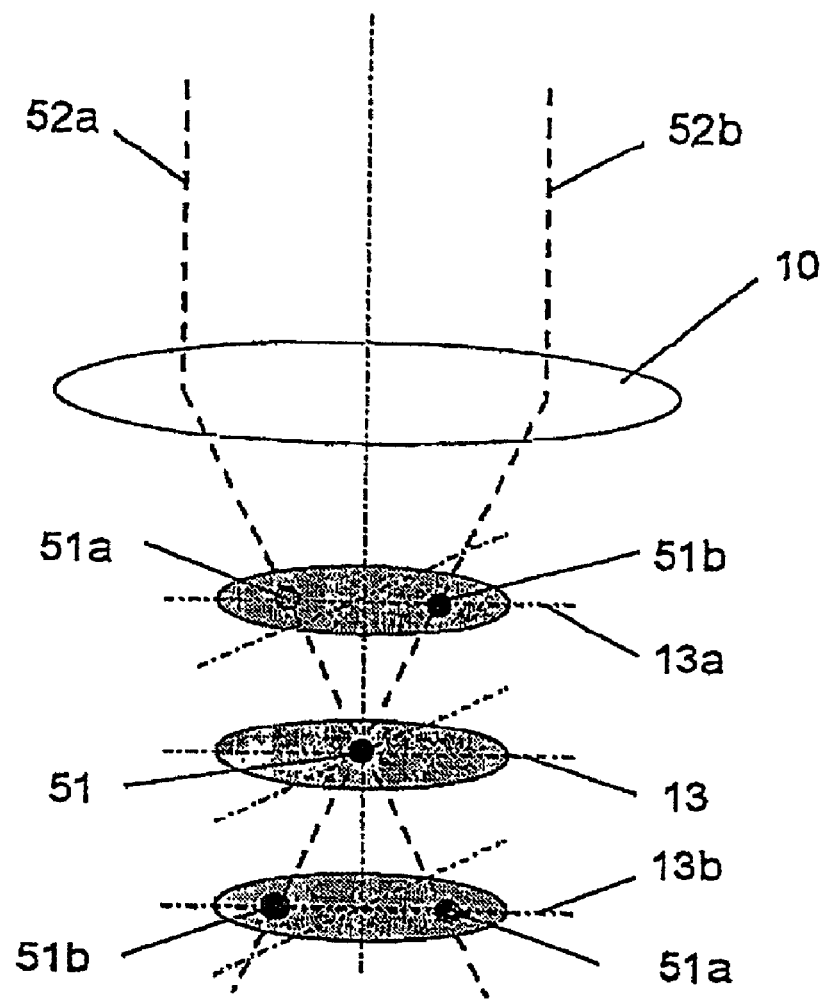
FIG. 3: A schematic profile of an inserted point-like pattern.

FIG. 3 shows the profile of an inserted point-like pattern 52a, 52b, the primary objective 10, the focused pattern 51, the defocused pattern elements 51a, 51b as well as the focal plane 13, for example the object surface, and the defocused planes 13a, 13b.

Figures 4A, 4B:
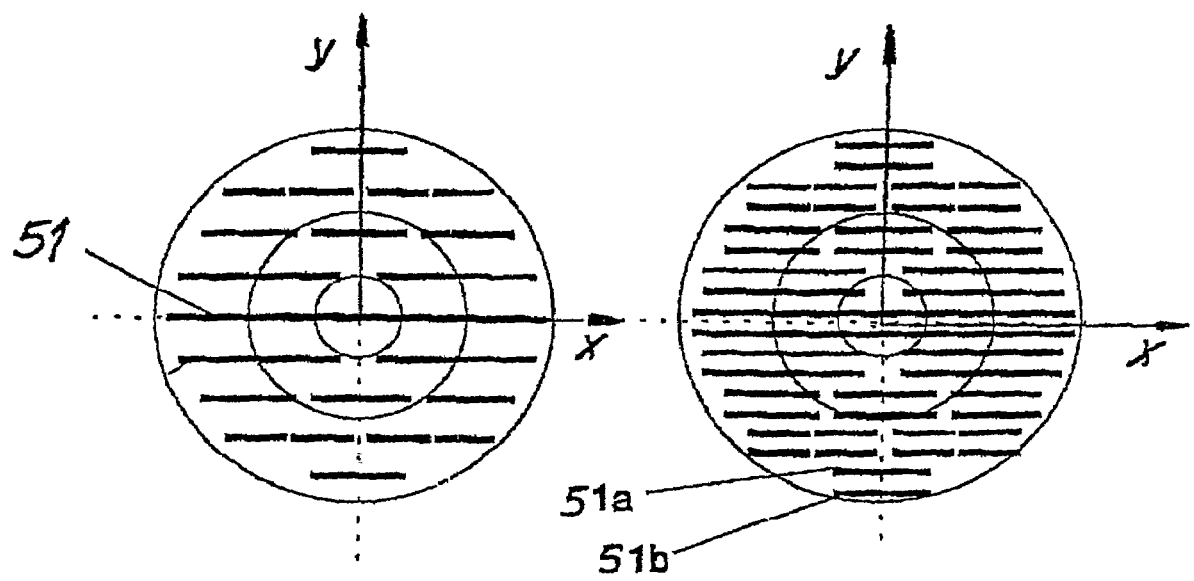
FIG. 4a: A focused line pattern.
FIG. 4b: A conjugate pattern element of a defocused line pattern.

FIG. 4a conceptually shows a focused line pattern 51; the pattern elements 51a and 51b lie precisely above one another. FIG. 4b shows the conjugate pattern elements 51a, 51b of a defocused line pattern.

Figure 5:
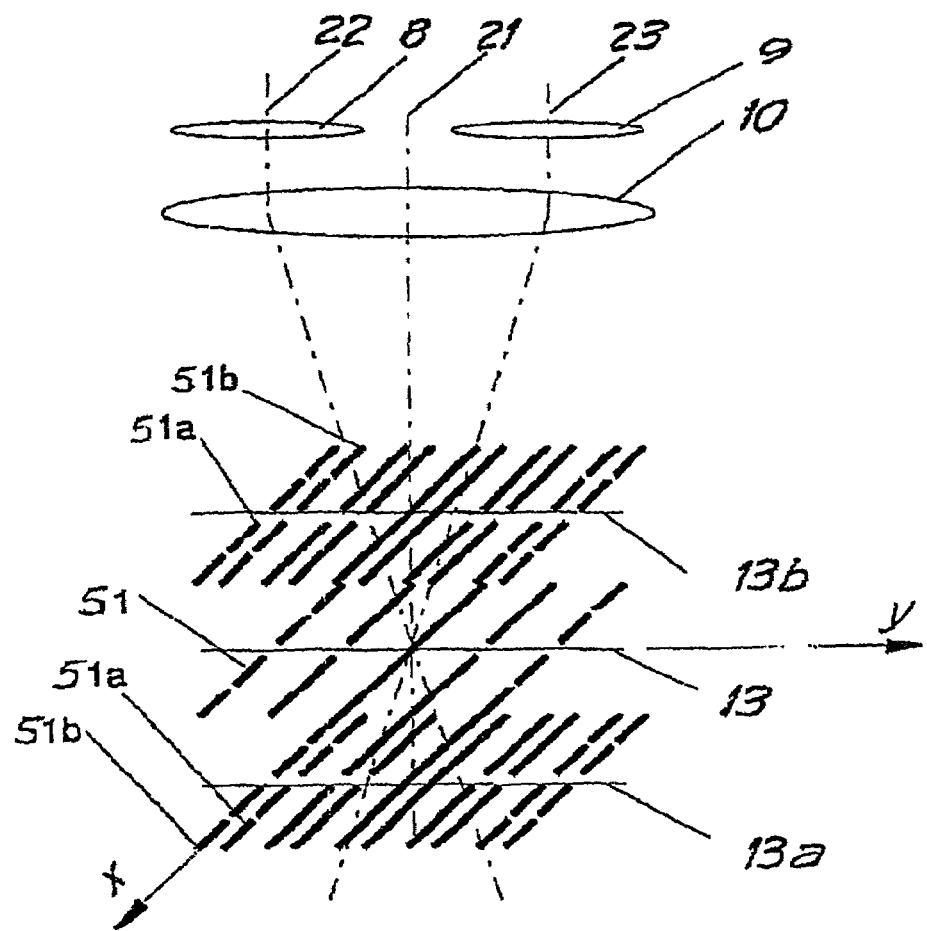
FIG. 5: A pattern projection in various focal planes.

In FIG. 5, the line pattern conceptually shown in FIG. 4 is schematically represented with the focal plane 13, the defocused planes 13a, 13b as well as the focused pattern 51/defocused patterns 51a, 51b.

Figure 6:
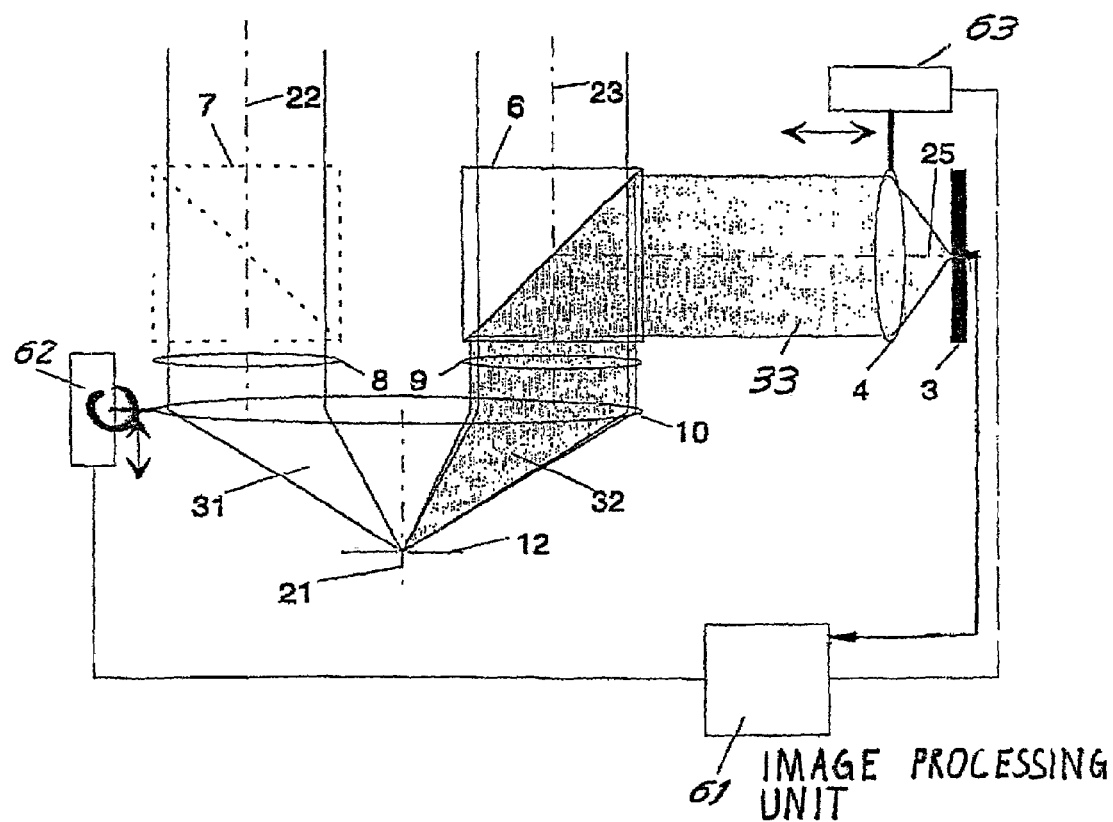
FIG. 6: A control loop of the focusing instrument for the primary objective and of the focusing instrument for the camera.

FIG. 6 schematically shows the control loop, comprising a camera 3, an image processing unit 61 for calculating the effective focal point from the current focus parameters of the primary objective 10 and the camera objective 4, a focusing instrument 62 for the primary objective 10 as well as a focusing instrument 63 for the optics 4 of the camera 3.

Figure 7:
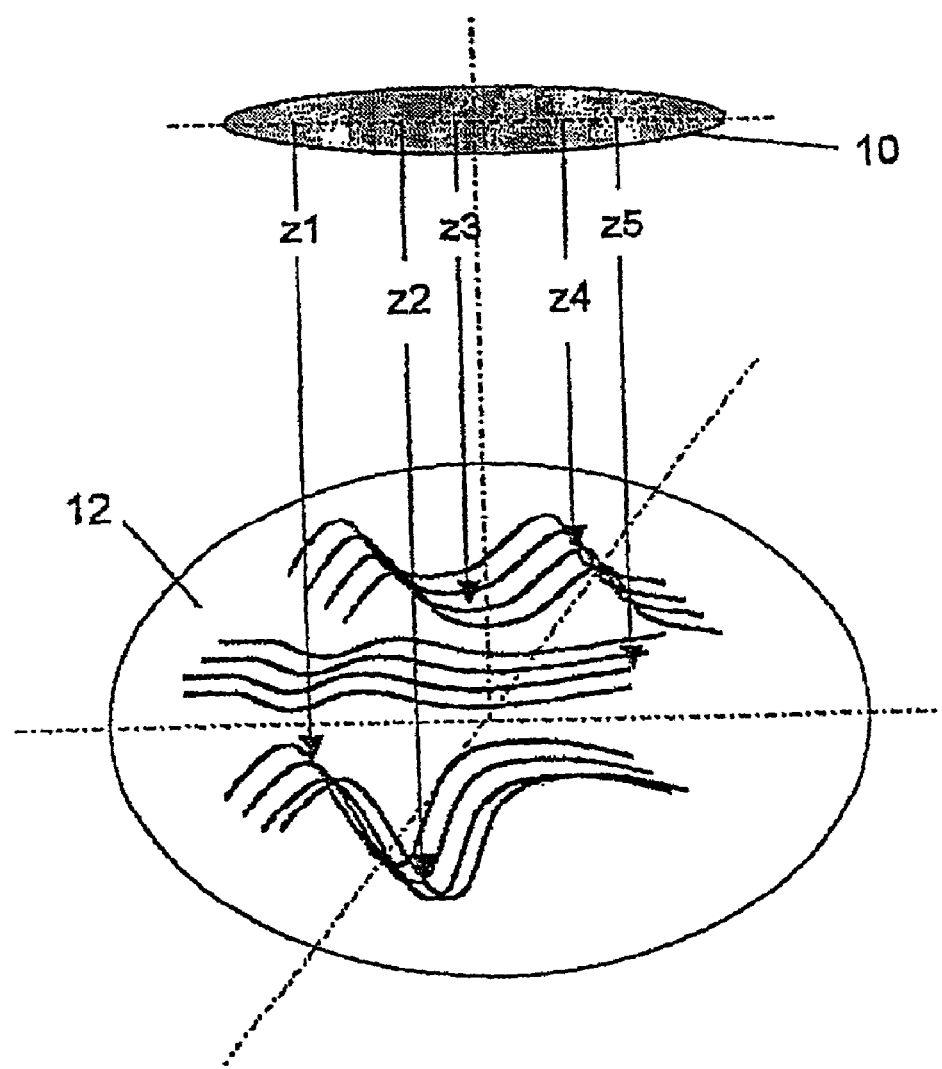
FIG. 7: An object surface and various distances z1 to z5 from the primary optics, which are to be detected.

FIG. 7 conceptually shows an object surface 12 and various distances z1 to z5 from the primary optics 10, which are to be detected.

Figure 8:
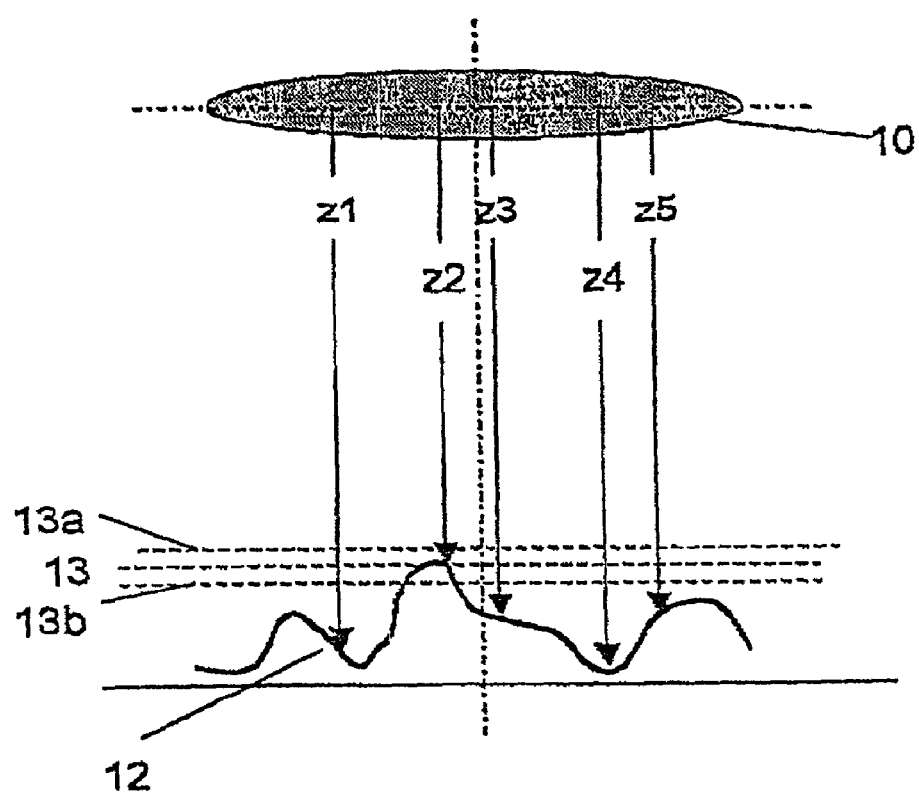
FIG. 8: An object surface and various distances z1 to z5 from the primary optics, which are to be detected as well as a focal plane and two defocused planes.

FIG. 8 shows, similarly to FIG. 7, an object surface 12, various distances z1 to z5 from the primary optics 10, which are to be detected, as well as the focal plane 13, for example relating to z2, as well as the defocused planes 13a, 13b.

Function

In a pattern generator 1, an optical pattern 51 is produced which is inserted, by means of beam splitters 6, 7, into the left and/or the right beam path 31, 32 of an optical observation instrument, for example a stereo operation microscope. The pattern consists of at least two points, although it ideally consists of two-dimensional line or grid patterns. The pattern is projected onto the object 12 via the primary objective 10. The reflection, or scattering, of the pattern from object 12 is in turn detected via the primary optics 10 and the beam splitters 6, 7, optics 4 and a camera 3, for example a CCD (FIG. 1).

When the pattern is focused accurately onto the focal plane 13, the pattern 51 appears as a single point, or a single line or a pattern (FIGS. 3-5). In the event of defocusing, the pattern 51a, 51b is seen double in the form of two conjugate points or conjugate lines or conjugate patterns (FIGS. 3-5).

The recognition of the conjugate patterns 51a, 51b is carried out via temporal and/or spatial and/or geometrical and/or spectral encoding of the pattern for the left and right beam path (31 and 32). On the basis of knowledge of the beam path, it is possible to calculate, from the two patterns, the distance z of one or more object points from the primary objective. With knowledge of the distances, direct focusing onto any desired object point f=z(x,y) is possible. Temporal encoding may be carried out, for example, by encoding the pattern 51 using a rotating shutter 11. The conjugate signals are separated by subtracting the normal image signal from the overall signal, respectively with the pattern 51a, 51b of the right and the left beam path. In a system unit 61, the relation of conjugate pattern elements is determined by suitable algorithms, and the primary objective—object distance z1 to z5 is computationally identified point-wise (FIG. 7, FIG. 8).

Once the produced and imaged pattern 51 has been two-dimensionally formed, then the surface structure of the object 12 can be computationally identified. This makes it possible to focus the focal plane 13 with respect to the structure of the object surface 12 or individual object points.

The focusing onto the defined focal plane 13 is carried out by means of an already well-known focusing instrument.

The selection of the object point to be defined may be carried out electronically—for example using the eye's line of sight, by analysing the movements of an instrument in the image field, using a joystick, a mouse pointer or the like—or it may be manually predefined.

In a particular refinement of the invention, separately focusable optics are placed in front of the camera 3, so that focusing changes of the measurement system do not need to be carried out via the primary objective. This permits focusing, which is independent of the primary beam path, for a second observer (FIG. 6) and/or focus determination which is independent of the primary beam path. In this case, the focus parameters of both optical systems are taken into account when calculating the object distances.

Overall, owing to the facility of producing a separate light pattern, the measurement system can be used virtually irrespective of the properties of the object.

| LIST and LEGEND | |
|---|---|
| 1 | pattern generator |
| 2 | optics for (1) |
| 3 | camera (e.g. CCD) |

-continued

LIST and LEGEND

| | |
|---|---|
| 4 | optics for (3) |
| 5 | beam splitter (1) |
| 6 | beam splitter of right beam path |
| 7 | beam splitter of left beam path |
| 8 | zoom optics of left beam path |
| 9 | zoom optics of right beam path |
| 10 | primary objective |
| 11 | shutter (rotating) |
| 12 | object surface |
| 13 | focal plane (object) |
| 13 a, b | positively and negatively defocused planes |
| 21 | optical axis of (10) |
| 22 | optical axis of left beam path |
| 23 | optical axis of right beam path |
| 24 | optical axis of (1) |
| 25 | optical axis of (3) |
| 30 | beam path of (1) |
| 31 | left beam path |
| 32 | right beam path |
| 33 | beam path of camera/CCD |
| 51 | focused pattern |
| 51 a, b | conjugate pattern elements (defocused patterns) |
| 52 a, b | inserted point-like pattern |
| 61 | image processing unit |
| 62 | focusing unit for (10) |
| 63 | focusing unit for (3) |
| Z1-Z5 | distances between (10) and (12) |

What is claimed is:

1. A method for determining a plurality of Z distances from an object surface to a reference plane of a microscope, comprising:
   obtaining a stereo microscope including a primary objective and two beam paths that pass through the primary objective;
   producing a pattern with a pattern generator;
   projecting the pattern into at least one of the two beam paths, through the primary objective, and onto an object, wherein the projected pattern exits the primary objective in a direction towards the object and at an angle with respect to an optical axis of the primary objective;
   detecting an image of the pattern with a camera;
   determining a plurality of Z distances based on the detected image of the pattern; and
   outputting at least one of the Z distances to a system,
   wherein the produced pattern is selected from the group consisting of a plurality of points, a plurality of beams, a plurality of lines, and a grid.

2. The method of claim 1, wherein the camera includes a CCD.

3. The method of claim 1, further comprising processing the image with an image processing unit.

4. The method of claim 1, wherein the Z distances are distances from the reference plane to the object.

5. The method of claim 4, wherein the reference plane is a primary plane of the primary objective of the stereo microscope.

6. The method of claim 1, wherein the Z distances are distances from the reference plane to a focal plane.

7. The method of claim 6, wherein the reference plane is a primary plane of the primary objective of the stereo microscope.

8. The method of claim 1, further comprising detecting and computationally identifying pattern elements using a predetermined mathematical algorithm.

9. The method of claim 6, further comprising locating the focal plane by determining the separation between a plurality of pattern elements.

10. The method of claim 1, wherein the pattern covers at least a portion of an observer's entire field of view.

11. The method of claim 1, wherein the colour of the pattern lies in the visible light-wavelength range.

12. The method of claim 1, wherein the colour of the pattern lies in the invisible light-wavelength range.

13. The method of claim 1, wherein the pattern is an encoded pattern selected from the group consisting of a temporally encoded pattern, a spatially encoded pattern, a geometrically encoded pattern, and a spectrally encoded pattern.

14. The method of claim 1, wherein the pattern comprises a plurality of encoded patterns selected from the group consisting of a temporally encoded pattern, a spatially encoded pattern, a geometrically encoded pattern, and a spectrally encoded pattern.

15. The method of claim 13, wherein the Z distances are determined using the encoded pattern.

16. The method of claim 1, wherein a Z distance is a distance from the reference plane to a focal plane that is computationally determined on the basis of a distance between the pattern elements, and further comprising focusing on the focal plane with a focusing instrument, wherein focusing is performed manually by observing the patterns.

17. The method of claim 1, wherein the Z distances are outputted to an external system.

18. The method of claim 1, further comprising identification of a focal value of a point and outputting the value as a distance parameter.

19. The method of claim 1, further comprising identification of a focal value of an area and outputting the value as a distance parameter.

20. The method of claim 1, further comprising identification of a focal value of a structure and outputting the value as a distance parameter.

21. The method of claim 1, wherein the pattern comprises conjugate pattern elements.

22. The method of claim 6, wherein a sign of deviation from the focal plane is identified through encoding.

23. The method of claim 1, wherein the plurality of Z distances are determined effectively simultaneously.

24. The method of claim 1, further comprising determining an altitudinal topography of the object surface with respect to the reference plane utilizing the plurality of determined Z distances.

25. The method of claim 1, wherein pattern elements substantially span the entire object surface viewed through the primary objective, further comprising determining the Z distances when at least a portion of the object surface is in a focal plane and at least a portion of the object surface is not in the focal plane, wherein the Z distances are determined for both the portion of the object surface in the focal plane and for the portion of the object surface not in the focal plane.

26. The method of claim 1, wherein the plurality of Z distances are obtained based on a single projection, the single projection including the pattern projected onto the object, and wherein the microscope is stationary with respect to the object while executing the method.

27. A method for determining a plurality of Z distances from an object surface to a reference plane of a microscope, comprising:
   obtaining a stereo microscope including a primary objective and two beam paths that pass through the primary objective;
   producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern; and outputting at least one of the Z distances to a system, wherein the Z distances are computationally determined on the basis of a distance between pattern elements.

28. The method of claim 27, wherein the pattern elements span the entire object.

29. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern; and outputting at least one of the Z distances to a system, wherein the Z distances are distances from the reference plane to a focal plane that is computationally determined on the basis of a distance between pattern elements, and further comprising automatically focusing on the focal plane with a focusing instrument based on at least one of the Z distances.

30. The method of claim 29, wherein focusing is performed in an electronically regulated fashion.

31. The method of claim 29, wherein focusing is performed in a beam path of a camera.

32. The method of claim 29, wherein focusing is performed in a continuous fashion.

33. The method of claim 29, wherein focusing is performed on instruction.

34. The method of claim 33, wherein the instruction is situation dependent.

35. The method of claim 31, wherein the method is performed for a video system.

36. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern;

outputting at least one of the Z distances to a system, and assigning pattern elements a code which permits identification of at least one pattern element.

37. The method of claim 36, wherein identification includes identifying pattern elements that belong together from a group that includes both (i) pattern elements that belong together and (ii) pattern elements that do not belong together.

38. The method of claim 36, wherein the code is formed from at least one light property selected from the group consisting of flashing light and light wavelength.

39. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern; and outputting at least one of the Z distances to a system, wherein pattern elements are alternately inserted into a left and right beam path of the two beam paths.

40. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern; and outputting at least one of the Z distances to a system, wherein pattern elements are respectively inserted into a right and left beam path of the two beam paths.

41. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern;

outputting at least one of the Z distances to a system, alternately temporally encoding a plurality of pattern elements; and obtaining a clean pattern of elements by subtracting a clean image signal.

42. A method for determining a plurality of Z distances from an object surface to a reference plane of a microscope, comprising:

obtaining a stereo microscope including a primary objective and two beam paths that pass through the primary objective;

producing a pattern with a pattern generator;

projecting the pattern into at least one of the two beam paths, through the primary objective, and onto an object, wherein the projected pattern exits the primary objective in a direction towards the object and at an angle with respect to an optical axis of the primary objective;

detecting an image of the pattern with a camera;

determining a plurality of Z distances based on the detected image of the pattern;

outputting at least one of the Z distances to a system, and temporally encoding at least one pattern element with a shutter.

43. The method of claim 42, wherein the shutter operates on at least one of a plurality of beam paths of the pattern.

44. The method of claim 42, wherein the shutter is a rotating disk with transmissive and non-transmissive regions.

45. A microscope including an instrument for determining Z distances, comprising:

a stereo microscope including a primary objective and two beam paths that pass through the primary objective;

a pattern-projector adapted to project an optical pattern into at least one of the two beam paths onto an object surface through the primary objective, wherein the microscope is adapted so that the optical pattern exits the primary objective in a direction towards the object and at an angle with respect to an optical axis of the objective;

a camera adapted to capture an image of the optical pattern on the object;

an electronic image processing unit adapted to determine a plurality of Z distances based on the image captured by the camera; and a recording device for recording projected patterns.

46. The microscope of claim 45, wherein the processing unit obtains recorded images from the recording device.

47. The microscope of claim 45, wherein the camera includes a CCD.

48. The microscope of claim 45, wherein the Z distances are distances from a reference plane to an object.

49. The microscope of claim 45, wherein the Z distances are computationally determined on the basis of a distance between pattern elements.

50. The microscope of claim 45, wherein the electronic image processing unit is adapted to determine the plurality of Z distances effectively simultaneously.

51. The microscope of claim 45, wherein the instrument is adapted to determine an altitudinal topography of the object surface with respect to the instrument utilizing the plurality of determined Z distances.

52. The microscope of claim 45, wherein the instrument is adapted to project the pattern so that the pattern substantially spans an entire object surface viewed through the primary objective, the instrument further being adapted to determine Z distances when at least a portion of the object surface is in a focal plane and at least a portion of the object surface is not in the focal plane, wherein the Z distances are determined for both the portion of the object surface in the focal plane and for the portion of the object surface not in the focal plane.

53. The microscope of claim 45, wherein the microscope is adapted to obtain the plurality of Z distances based on a single projection, the single projection including the optical pattern projected onto the object, while the microscope is stationary with respect to the object.

54. A microscope including an instrument for determining Z distances, comprising:

a stereo microscope including an objective and two beam paths that pass through the objective;

a pattern-projector adapted to project an optical pattern into at least one of the two beam paths, through the objective, and onto an object surface through separate optics;

a camera adapted to capture an image of the optical pattern on the object, wherein the microscope is adapted so that the optical pattern exits the objective in a direction towards the object and at an angle with respect to an optical axis of the objective; and an electronic image processing unit adapted for determining a plurality of Z distances based on the image captured by the camera, wherein the electronic image processing unit is adapted to determine the plurality of Z distances effectively simultaneously.

55. The microscope of claim 54, wherein the instrument is adapted to determine an altitudinal topography of the object surface with respect to the instrument utilizing the plurality of determined Z distances.

56. The microscope of claim 54, wherein the instrument is adapted to project the pattern so that the pattern substantially spans an entire object surface viewed through the objective, the instrument further being adapted to determine Z distances when at least a portion of the object surface is in a focal plane and at least a portion of the object surface is not in the focal plane, wherein the Z distances are determined for both the portion of the object surface in the focal plane and for the portion of the object surface not in the focal plane.

57. The microscope of claim 54, wherein the microscope is adapted to obtain the plurality of Z distances based on a single projection, the single projection including the optical pattern projected onto the object, while the microscope is stationary with respect to the object.

58. A microscope system for determining Z distances, comprising:

a microscope including a primary objective;

a pattern-projector adapted to project an optical pattern onto an object surface through separate optics, wherein the microscope is adapted so that the optical pattern exits the primary objective in a direction towards the object and at an angle with respect to an optical axis of the objective;

a camera adapted to capture an image of the optical pattern on the object; and an electronic image processing unit adapted for determining a plurality of Z distances based on the image captured by the camera, wherein the electronic image processing unit is adapted to determine the plurality of Z distances effectively simultaneously.

59. The microscope system of claim 58, wherein the microscope is adapted to determine an altitudinal topography of the object surface with respect to the microscope utilizing the plurality of determined Z distances.

60. The microscope system of claim 58, wherein the microscope is adapted to project the pattern so that the pattern substantially spans an entire object surface viewed through the primary objective, the instrument further being adapted to determine Z distances when at least a portion of the object surface is in a focal plane and at least a portion of the object surface is not in the focal plane, wherein the Z distances are determined for both the portion of the object surface in the focal plane and for the portion of the object surface not in the focal plane.

61. The microscope of claim 58, wherein the microscope is adapted to obtain the plurality of Z distances based on a single projection, the single projection including the optical pattern projected onto the object, while the microscope is stationary with respect to the object.

* * * * *